United States Patent [19]

Ghenassia et al.

[11] Patent Number: 4,484,009

[45] Date of Patent: Nov. 20, 1984

[54] PROCESS FOR THE MANUFACTURE OF GLYCOL MONOETHERS

[75] Inventors: Elie Ghenassia; André Lakodey, both of Chocques, France

[73] Assignee: Atochem, Courbevoie, France

[21] Appl. No.: 481,835

[22] Filed: Apr. 4, 1983

[30] Foreign Application Priority Data

Apr. 20, 1982 [FR] France ................................ 82 06728

[51] Int. Cl.$^3$ ............................................. C07C 41/00
[52] U.S. Cl. .................................... 568/678; 568/662; 568/670; 568/671; 568/672
[58] Field of Search ............... 568/670, 671, 672, 678, 568/662

[56] References Cited

U.S. PATENT DOCUMENTS 4,088,700  5/1978  Watts ................................... 568/671

FOREIGN PATENT DOCUMENTS 1020500  2/1966  United Kingdom ................ 568/678

OTHER PUBLICATIONS

Cabanac et al., Academie des Sciences, Reports, vol. 188, No. 19, pp. 1257–1259.

Primary Examiner—Howard T. Mars
Attorney, Agent, or Firm—Sigalos & Levine

[57] ABSTRACT

A process for the manufacture of the monoether of monoethylene glycol by the hydrogenolysis of a 2-alkyl-1,3-dioxolane, with a co-catalytic system of palladium and an acid of phosphorus or a phosphoric ester of ethylene glycol and in the presence of ethylene glycol.

8 Claims, No Drawings

PROCESS FOR THE MANUFACTURE OF GLYCOL MONOETHERS

BACKGROUND OF THE INVENTION

The present invention concerns a selective process for the manufacture of glycol monoethers and more particularly the monoethers of monoethyleneglycol.

Presently, the manufacture of these products takes place in known manner, by reaction between an alcohol and ethylene oxide, in the liquid phase, in the presence of a catalyst. In this type of procedure, the monoether of the monoethyleneglycol formed has the same reactivity with respect to the ethylene oxide as does the initial alcohol, and reacts, as soon as it has been formed, competitively with the alcohol, with ethylene oxide in order to yield the monoether of diethyleneglycol which, in its turn leads to the formation of the monoether of the oligoethyleneglycols following a statistical distribution. Furthermore, the proportion of these derivatives of oligoethyleneglycol increases considerably with the molecular weight of the alcohol being used, so that it is impossible industrially to ensure a manufacture of the monoethers of monoethyleneglycol derived from alcohols comprising more than two carbon atoms without formation of considerable amounts of by-products.

The hydrogenolysis (destructive hydrogenation) of open acetals leads to the simultaneous and equimolecular formation of ether and of alcohol according to the reaction:

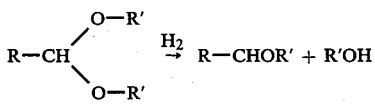

This reaction has been known since the work of CABANAC —Reports of the French Academy of Sciences—1929—first semester—Vol. 188—No. 19, page 1251. French Patent No. 2,422,614 describes an improved procedure for the hydrogenolysis of acetals and of ketals of organic hydrocarbons, by operating in the presence of a catalyst composed of a halide of an element of Group III A of the Periodic Table, such as AlCl$_4$, BF$_3$, etc. and of a hydrogenation catalyst constituted solely of platinum or of rhodium having been deposited on a support, in the liquid phase, at a temperature between $-15°$ and $+125°$ C., and under a pressure between 3.5 and 140 atmospheres.

SUMMARY OF THE INVENTION

According to the invention, it is possible to manufacture the 2-alkoxy ethanols of the general formula R—O—CH$_2$—CH$_2$OH in selective manner by the hydrogenolysis of the acetals derived from ethyleneglycol and linear or branched aliphatic aldehydes or alkylcycloaliphatics, corresponding to Group R, and comprising between 1 to 12 carbon atoms.

The acetals which make it possible to simultaneously obtain the best conversion rates and high selectivities are the alkyldioxolanes produced by the reaction between an aldehyde R—CHO and a vicinal diol, more particularly ethyleneglycol. These acetals present the cyclic structure of a 2-alkyl-1,3-dioxolane as follows:

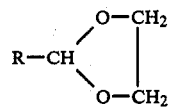

in which R is a hydrocarbon group which can be saturated aliphatic, linear or branched, cycloaliphatic or aromatic, unsubstituted or substituted by other hydrocarbon groups, with the number of carbon atoms of the principal chain being between 1 to 12, and the number of carbon atoms of each of the substituents being between 1 and 4. In practice, R is hydrogen or a methyl, ethyl, propyl, isopropyl, butyl, isobutyl, tertiobutyl, pentyl, hexyl, heptyl, octyl, or the like radical, or one of their isomers, whether unsubstituted or substituted. R can also be an alicyclic radical such as cyclohexyl, cyclohexenyl, or the like, unsubstituted or substituted, or an aromatic benzyl or tolyl group, and the like.

The hydrogenolysis of the 2-alkyl-1,3-dioxolanes takes place, in the liquid phase, in the presence of a co-catalytic system constituted by a hydrogenation catalyst and an acid catalyst, with the first one functioning as a heterogeneous catalyst and the second one being either adsorbed on the support of the preceding one or on any other support, or being dissolved in the mixture to be hydrogenolyzed, or an equilibrium between the two phases, and proceeds according to the well-known principles of homogeneous acid catalysis.

DETAILED DESCRIPTION

They hydrogenation catalysts, generally speaking, are the transition metals of Group VIII of the Periodic Table. It has, however, been observed that in the case of the present invention the hydrogenolysis must take place in the presence of palladium, since the other metals of Group VIII do not make it possible to obtain an industrially interesting result. The palladium can be introduced into the reaction medium as is, as a finely divided powder, or deposited on a support like alumina, carbon, silica, titanium oxide, Kieselguhr and other such known supports.

The acid catalyst associated with the palladium is selected from among the acids of phosphorus such as phosphoric acid, pyrophosphoric acid, metaphosphoric acid, phosphoric acid, alkyl phosphoric acid, or even phosphoric esters, including pyrophosphoric esters, of ethylene glycol. Although other strong acids have been tried as palladium co-catalysts, it has not been possible to obtain an industrially interesting result.

With the co-catalytic system of palladium/acid of phosphorus it is possible to obtain, under the best operating conditions, excellent conversion rates of 2-alkyl-1,3-dioxolanes, which can often be above 99%, and high selectivities, often above 95% of the monoether of monoethylene glycol.

The hydrogenolysis reaction of the 2-alkyl-1,3-dioxolanes is conducted in the liquid phase, in the presence of ethylene glycol as the solvent. It has been observed that the use of a solvent other than ethylene glycol involves the formation of by-products which in appreciable manner limit the selectivity of the reaction and reduce the yield of monoether of monoethyleneglycol and can render more difficult the separation by distillation of the desired glycol ethers. The quantities of ethylene glycol which it is desirable to use vary as a function of the molecular mass of the 2-alkyl dioxolane to be hydrogenolyzed. The molar ratio of monoethylene glycol to 2-alkyl-1,3-dioxolane can vary between 1 and 15, preferably must be located between 1 and 10, which permits, at the same time, a high selectivity and an interesting, high industrial productivity in glycol monoether.

The quantity of palladium necessary for the hydrogenolysis is not critical, however; although no harmful effect appears, it is not advantageous to use too large an excess of catalyst. It is recommended to have a palladium concentration in relation to the total mass of the mixture of 2-alkyl-1,3-dioxolane and ethylene glycol between 50 and 1,500 ppm and preferably between 100 and 1,000 ppm.

The content of acid of phosphorous or of phosphoric ester of monoethylene glycol reported as $H_3PO_4$ (orthophosphoric acid) can vary between 0.01 and 0.75% and preferably between 0.02, and 0.5% of the mass of the mixture of acetal/ethylene glycol.

It appears that the use of a stabilizer of the hydroquinone family at a rate of 0.0005 to 0.005% by weight and particularly of 0.001 to 0.003% in relation to the weight of the mixture of alkyldioxolane/solvent, exerts a beneficial influence on the selectivity in monoether of monoethylene glycol; with the quantity of by-products other than the 1,2 dibutoxy ethane, for instance, formed during the hydrogenolysis of 2-propyl-1,3-dioxolane capable of being divided by a factor of 2 to 3.

The most favorable hydrogenolysis temperatures vary between 100° and 250° C. It is however preferred to operate between 150° and 200° C. in such a way as to obtain the best convestion rates of the 2-alkyl-1,3-dioxolanes in a short time and without using excessively large quantities of catalyst.

The hydrogen pressure in the reactor can vary between 20 and 150 bars, although pressures of 30 to 100 bars are preferable. Under these conditions, by operating discontinuously, the duration of hydrogenolysis does not exceed durations of the order of 3 to 5 hours.

The preparation of the dioxolanes can take place according to one of numerous known methods. The simplest method consists of ketalizing an aldehyde R—CHO with ethylene glycol, with elimination of the water formed in the reaction by standard means of fractional or azeotropic distillation or with the help of a drying agent. The mixtures of aldehydes having the structure of R—CHO, with R being one of the previously defined alkyl radicals, and of ethylene glycol can be hydrogenolyzed in situ following an agitation period of 2 to 3 hours at a temperature of 80° to 100° C. in an inert atmosphere.

The hydrogenolysis is conducted according to the previously cited temperature and pressure conditions, after the introduction of hydrogen, with the co-catalytic system and possibly hydroquinone having been introduced initially into the reactor with the mixture of aldehyde/ethylene glycol. The reaction products are principally constituted of glycol monoether and of alkyl dioxolane derived from the aldehyde. The alcohol likely to be formed by the direct hydrogenation of the aldehyde and in spite of the presence of water is encountered only in slight quantity.

The glycol ether contained in the reaction mixture after hydrogenolysis can be separated from the other constituents by all known standard means such as, for instance, fractional distillation after the elimination of the heterogeneous catalyst by filtration.

The invention will be further described in connection with the following examples which are set forth for purposes of illustration and comparison only.

EXAMPLE 1

Into an autoclave made of stainless steel (NSMC) and having a capacity of 1 liter and being mechanically agitated, there is introduced 250 g of ethylene glycol and 50 g (0.431 moles) of 2-propyl-1,3-dioxolane (PDX):

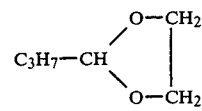

with 1 g of catalyst composed of 5% by weight of palladium deposited on alumina, 180 mg of concentrated phosphoric acid, and 3 mg of hydroquinone. After having purged the autoclave with nitrogen, the latter is pressurized with hydrogen in such a way that the internal pressure reaches 100 bars at a temperature of 150° C. The pressure is then adjusted to 100 bars with hydrogen according to need, by maintaining the temperature at 150° C. for 3 hours. After cooling, the autoclave is emptied and the reaction medium is filtered under nitrogen atmosphere. An analysis by gas phase chromatography of the filtrate shows that the total conversion rate of 2-propyl-1,3-dioxolane reaches 99.2%. The weight of 2-butoxy-1-ethanol having been formed amounts to 48.5 g (0.411 moles) and the weight of 1,2-dibutoxy ethane amounts to 1.36 g (0.0078 moles).

EXAMPLE 2

(Comparative Example)

The procedure of Example 1 was followed except that there was used 1 g of catalyst composed of 5% by weight of rhodium on an alumina support, in the presence of 180 mg of concentrated phosphoric acid. The hydrogenolysis of 50 g of 2-propyl-1,3-dioxolane in the presence of 250 g of ethylene glycol containing 3 mg of hydroquinone, after 3 hours of agitation under a pressure of 100 bars at a temperature of 200° C. and filtration, yields a conversion rate of the propyl dioxolane (PDX) of only 57%.

The reaction mixture contains 14.7 g of 2-butoxy-1-ethanol and 5.6 g of normal butanol.

EXAMPLES 3 and 4

(Comparative Examples)

The tests corresponding to these examples are carried out under the conditions of Example 1, except that for each one of them there is used 1 g of catalyst composed of platinum deposited on alumina at a rate of 5% by weight, or nickel deposited on kieselguhr at a rate of 50% of nickel by weight.

The following table regroups the quantities of the principal products obtained.

|  | Example No. 3 | Example No. 4 |
|---|---|---|
| Hydrogenation Catalyst | Pt/Al$_2$O$_3$ | Ni/kieselguhr |
| Co-catalyst | H$_3$PO$_4$ | H$_3$PO$_4$ |
| Conversion Rate (Degree of Conversion) of PDX (%) | 38 | 51.6 |
| Weight of 2-butoxy ethanol (g) | 4.98 | 11.3 |
| Weight of butanol (g) | 5 | 6.4 |

EXAMPLE 5

Operating according to the conditions of Example 1, 50 g (0.43 moles) of 2-propyl-1,3-dioxolane and 250 g of ethylene glycol are hydrogenolyzed in the presence of the catalytic pair composed of 5 g of palladium deposited on titanium oxide at a rate of 0.2% by weight, and 180 mg of concentrated phosphoric acid. The yield of 2-butoxy-1-ethanol reaches 92%.

EXAMPLE 6

Into the autoclave having 1-liter capacity as used in Example 1, there are introduced 50 g of 2-propyl dioxolane and 250 g of ethylene glycol and then 80 mg of pyrophosphoric acid, $H_4P_2O_7$, and 1 g of hydrogenation catalyst, $Pd/Al_2O_3$, at 5% of active metal by weight and 0.009 g of hydroquinone. After purging with nitrogen, the autoclave is pressurized under a pressure of 100 bars of hydrogen at a temperature of 170° C. This pressure is maintained for 3 hours under agitation at 170° C. After filtration, chromatographic analysis shows that 99.7% of propyl dioxolane have been converted. The degree of conversion of

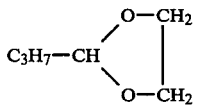

into 2-butoxy-1-ethanol (expressed in moles) attains 90.6%, or 46.1 g, with the quantities of 1,2-dibutoxy ethane and of normal butanol respectively amounting to 2.21 and 1.35 g.

EXAMPLE 7

(Comparative Example)

Operating according to the conditions of Example 1, the hydrogenolysis of 50 g of 2-propyl-1,3-dioxolane in the presence of 250 g of monoethylene glycol is carried out in the presence of 1 g of palladium catalyst deposited on alumina in a proportion of 5% of active metal by weight. The co-catalyst used is para-toluenesulfonic acid at a rate of 0.72 g per 300 g of the mixture of PDX/ethylene glycol containing 6 mg of hydroquinone. Under a hydrogen pressure of 100 bars, the autoclave is agitated for 3 hours, by keeping the temperature at 150° C. The quantity of 2-butoxy-1-ethanol formed amounts to 37.5 g (0.318 moles), while the quantities of 1,2-dibutoxy ethane and normal butanol, respectively, are 1.6 g (0.0091 moles) and 0.5 g (0.0067 moles). The use of paratoluene sulfonic acid as co-catalyst involves the information of large quantities of high-molecular weight by-products, among which are 6.7 g of diethylene glycol.

EXAMPLES 8 to 12

(Comparative Examples)

In this series of examples, the tests carried out with various mineral or organic acids have been summarized below. The quantities of reactants; i.e., propyl dioxolane, ethylene glycol, hydroquinone and hydrogenation catalysts of palladium (Pd) on carbon in the proportion of 5%, are identical to the quantities utilized in Example 6. The duration of hydrogenolysis amounts to 3 hours and the hydrogen pressure amounts to 100 bars. The particular conditions and the results have been reassembled in the following general table.

| Example No. | Acid catalyst | Acid weight (g) | T° C. | Degree of conversion of the PDX (%) | TT into butoxy ethanol (%) | TT % into dibutoxy ethane | TT % into butanol |
|---|---|---|---|---|---|---|---|
| 8 | HCl | 0.18 | 170 | 83.9 | 71 | 4.2 | 5.2 |
| 9 | HCOOH | 0.18 | 100 | 28.7 | 24.1 | 0.3 | 2.2 |
| 10 | Phosphonic benzene | 0.18 | 170 | 66 | 44 | 1.4 | — |
| 11 | $CF_3COOH$ | 0.18 | 170 | 65 | 60.3 | 3.2 | 0.2 |
| 12 | COOH\|COOH | 0.18 | 170 | 11.5 | 8.8 | — | 1.3 |

TT % = molar degree of conversion of the PDX into one of the reaction products.

EXAMPLE 13

A mixture of ethylene glycol (250 g)/concentrated phosphoric acid (180 mg) is heated for 3 hours at 170° C. Chemical analysis shows that the acid introduced has been esterified by the ethylene glycol. This mixture is introduced into the reactor with 50 g of PDX and hydrogenolyzed in the presence of 1 g of palladium deposited on carbon and 0.009 g of hydroquinone, at a temperature of 170° C. under 100 bars of hydrogen pressure for 3 hours. After cooling and filtration, analysis shows that 96% of the PDX have been converted and that 90% have been converted into 2-butoxy-1-ethanol. The quantity of dibutoxy ethane reaches 1.74 g (0.01 mole).

EXAMPLE 14

The mixture of 50 g of

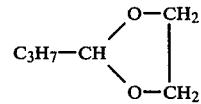

and 250 g of $CH_2OH-CH_2OH$ is hydrogenolyzed in the presence of a catalytic system constituted of 1 g of palladium deposited on alumina at a rate of 5% of Pd by weight, 88 mg of orthophosphoric acid concentrated to 85%, and 3 mg of hydroquinone. After 7 hours of agitation at a temperature of 185° C. under a hydrogen pressure kept constant at 100 bars, 97.3% of the propyl dioxolane are converted, 47.2 g (0.4 moles) of 2-butoxy-1-ethanol are determined, as well as very slight quantities of butanol (0.008 moles) and of 1,2-dibutoxy ethane (0.003 moles).

EXAMPLE 15

A mixture of 50 g of

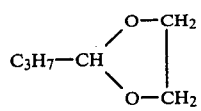

and 250 g of ethylene glycol is hydrogenolized in a stainless steel autoclave, in the presence of a catalytic system consisting of 1 g of palladium having been deposited on alumina at a rate of 5% by weight of active metal, 1.76 g of $H_3PO_4$ at 85% concentration, and 9 mg of hydroquinone. After 7 hours of agitation at a temperature of 100° C. and under a pressure kept constant at 100 bars, 75.4% of propyl dioxolane have been converted. The degree of conversion into 2-butoxy-1-ethanol reaches 70.6% and the molar yield reaches 93.6%. The quantities of butanol and of 1-dibutoxy ethane respectively amount to 0.4 and 0.75 g.

EXAMPLE 16

(Comparative Example)

Into a reactor of 1-liter capacity, agitated mechanically, there is introduced 300 g (2.58 moles) of 2-propyl-1,3-dioxolane, titrating 99.8% purity, with 3 mg of hydroquinone, 1 g of palladium on alumina at a rate of 5% of Pd by weight, and 88 mg of phosphoric acid at 85% concentration. After pressurization with hydrogen, the autoclave is heated to 185° C. and the pressure is adjusted and kept at 100 bars for 3 hours. After cooling and filtration of the catalyst, the reaction mixture, analyzed by gas chromatography, contains 160 g (1.359 moles) of 2-butoxy-1-ethanol, 90.9g of 1,2-dibutoxy ethane (0.522 moles) and 33 g of ethylene glycol (0.53 moles) The molar degree of conversion of the PDX into $C_4H_9—O—CH_2—CH_2OH$ amounts to 52.7%.

EXAMPLE 17

Operating according to Example 16, a mixture to 50 g of 2-propyl-1,3-dioxolane and 250 g of ethylene glycol is hydrogenolyzed in an agitated reactor. The catalytic pair is composed of 1 g of Pd/Al$_2$O$_3$ containing 5% by weight of active metal and 200 mg of orthophosphoric acid at 85% concentration. After the addition of 3 ppm of hydroquinone, the autoclave is pressurized by hydrogen and the temperature is controlled at 150° C. The pressure is kept at 100 bars by an added amount of hydrogen, for 3 hours. After cooling and filtration, the reaction mixture is determined by gas phase chromotography. 99.2% of the propyl dioxolane is converted and the molar degree of conversion of this reactant into 2-butoxy-1-ethanol reaches 95.9%. The butanol content in the reaction mixture amounts to 0.31% and the butoxy-ethane content amounts to 0.12%.

EXAMPLE 18

(Comparative Example)

Operating according to Example 17, but replacing the ethylene glycol by normal butanol; 50 g (0.431 moles) of propyl dioxolane and 250 g of normal butanol (3.78 moles) are hydrogenolyzed. After 3 hours of agitation at 150° C. under 100 bars of hydrogen pressure, 98.9% of the acetal are converted and the molar degree of conversion (TT%) into 2-butoxy-1-ethanol reaches only 23.10% and the degree of conversion into the principal product, dibutyl ether, rises to 71.6%.

EXAMPLE 19

(Comparative Example)

Operating as in Example 17, but replacing the ethylene glycol by 2-butoxy-1-ethanol, after 3 hours at 150° C. under 100 bars of hydrogen pressure, 99.9% of

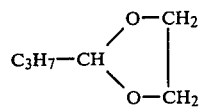

have been converted, and the degree of conversion of this reactant into 2-butoxy-1-ethanol reaches only 32.7% and the TT (degree of conversion) into the principal product, the 1,2-dibutoxy ethane, amounts to 62.2%.

EXAMPLE 20

Operating according to Example 17, a mixture submitted to hydrogenolysis contains 81.7 g (0.704) moles of 2-propyl-1,3-dioxolane and 218.3 g (3.521 moles) of ethylene glycol, which corresponds to a mole ratio of monoethylene glycol to acetal of 5. The catalytic pair is composed of 1 g of palladium deposited on carbon containing 5% by weight of Pd and 210 mg of orthophosphoric acid at 85% concentration. In the presence of 10 ppm of hydroquinone, after 3 hours of agitation at 150° C. under a hydrogen pressure kept constant at 100 bars, the degree of conversion of 2-propyl dioxolane reaches 99.9%, and 74.7 g of 2-butoxy-1-ethanol (TT 89.9%) are determined by chromatography. The degree of conversion of the propyl dioxolane into 1,2-dibutoxy ethane reaches 8.5% (5.2 g) and 2% of normal butanol (1.04 g).

EXAMPLE 21

Operating under the conditions of Example 17, a mixture subjected to hydrogenolysis contains 128.4 g (1.106 moles) of propyl dioxolane and 171.6 g of ethylene glycol, which corresponds to a molar ratio of $CH_2OH—CH_2OH$ to

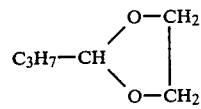

of 2.5. After 3 hours of agitation of 150° C. under a pressure kept constant at 100 bars of hydrogen and in the presence of the catalytic pair of 1 g of Pd/Al$_2$O$_3$ at 5% of palladium, and 210 mg of phosphoric acid at 85% concentration, the quantity of 2-propyl-1,3-dioxolane having been converted amounts to 117.5 g. The weight of 2-butoxy-1-ethanol formed reaches 108.2 g (TT 83.5%) and the weight of 1,2-dibutoxy ethane, the principal impurity, amounts to 8 g (0.046 moles).

EXAMPLE 22

Operation takes place according to Example 1, keeping all of the proportions of reactants and catalysts identical, but in the absence of hydroquinone. After 3 hours of reaction at 150° C. under 100 bars of hydrogen pressure, the autoclave is emptied and the reaction mixture is filtered under nitrogen atmosphere. Chromatographic analysis of the filtrate shows that the total degree of conversion of the 2-propyl-1,3-dioxolane reaches 99%. The weight of 2-butoxy-1-ethanol formed amounts to 47.6 g (0.403 moles) and the weight of dibutoxy ethane is 1.34 g. The degrees of molar conversion of the 2-propyl-1,3-dioxolane into other impurities, namely dibutyl ether, ethyl butyrate and normal butanol, respectively, attain 0.17, 1.1, and 1.72% as compared to 0.1, 0.2, and 1.05% in Example 1, which was carried out in the presence of 10 ppm of hydroquinone, in relation to the mixture of the reactants PDX/ethylene glycol.

EXAMPLE 23

Hydrogenolysis is carried out in an agitated reactor of 1-liter capacity, at a temperature of 200° C. under a constant pressure of 100 bars of hydrogen, for 7 hours, of a mixture composed of 50 g of 2-propyl-dioxolane and 250 g of ethylene glycol, yields 46.3 g (0.392 moles) of 2-butoxy-1-ethanol in the presence of the following pair: 1 g of palladium catalyst deposited on alumina at a rate of 5%, and 90 mg of phosphoric acid at 85% concentration. Under these conditions, the degree of conversion of the PDX reaches 97.2%.

EXAMPLE 24

The mixture consisting of 50 g (0.431 moles) of 2-propyl-1,3-dioxolane and 250 g of ethylene glycol is hydrogenolyzed in a mechanically agitated autoclave of 1-liter capacity, in the presence of 9 mg of hydroquinone, 5 g of palladium catalyst deposited on carbon at a rate of 5% of palladium by weight and of 210 mg of concentrated phosphoric acid. After 3 hours at a temperature of 170° C. under a hydrogen pressure kept constant at 30 bars, the degree of conversion of the 2-propyl dioxolane reaches 98.2%; 46.1 g (0.390 moles) of 2-butoxy-1-ethanol are produced besides 2.35 g (0.0135 moles) of 1,2-dibutoxy ethane and 0.31 g (0.004 moles) of normal butanol.

EXAMPLE 25

Into a stainless steel autoclave of 1-liter capacity, 67.6 g of 2-(3-cyclohexene) yl—1,3 dioxolane:

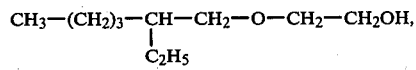

and 232.4 g of ethylene glycol are introduced with 9 mg of hydroquinone and a catalytic pair constituted of 2 g of palladium deposited on carbon at a rate of 2% of Pd by weight and 210 mg of orthophosphoric acid concentrated at 85%. After purging with nitrogen, the agitated reactor is heated under hydrogen to 170° C. The pressure is adjusted to 100 bars and kept constant for 3 hours. After cooling and filtration in order to eliminate the heterogeneous catalyst of palladium on carbon, the reaction mixture is analyzed by gas chromatography. 99.8% of the acetal have disappeared and 35.6 g of cyclohexane methyline oxy ethanol

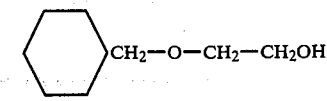

are determined by gas chromatography.

EXAMPLE 26

Operating according to the conditions of Example 24, hydrogenolysis of a mixture of 65 g (1'-ethyl) 2-pentyl-1,3-dioxolane and 235 g of ethylene glycol leads to a degree of conversion of the acetal into (2'-ethyl) 2-hexyloxy-1-ethanol, i.e., $$CH_3-(CH_2)_3-\underset{\underset{C_2H_5}{|}}{CH}-CH_2-O-CH_2-CH_2OH,$$

of 63.8% and a degree of conversion of the acetal of 78.8%.

EXAMPLE 27

Operating according to Example 24, hydrogenolysis of a mixture of 42.8 g (0.486 moles) of 2 methyl 7.3 dioxolane and 257.2 g of ethylene glycol leads to the formation of 40.5 g (0.45 moles) of 2-ethoxy-1-ethanol, the degree of conversion of the acetal being 99.8%.

EXAMPLE 28

The reactants 31.2 g of butyraldehyde (0.433 moles) and 268.8 g of ethylene glycol in a molar ration of 10 for 1, 9 mg of hydroquinone, 85% H₃PO₄ and palladium at 5% on alumina at a respective ratio of 600 ppm and 0.33% by weight of the mixture, are loaded into a stainless steel reactor, then heated under agitation for 3 hours at 100° C., the autoclave having previously been purged with nitrogen. Without opening the autoclave, the hydrogen is introduced under a pressure of 100 bars and hydrogenolysis is conducted at 185° C. for 2 hours by keeping the hydrogen pressure constant.

Following cooling and filtration, the reaction mixture is determined by gas phase chromatography. Under experimental conditions, the degree of conversion of the butyraldehyde reaches 99.2% and the degree of conversion of the ethylene glycol reaches 8.85% (99.4% of the theoretical quantity to be consumed). Analysis shows that the principal products having been formed are 2-butoxy-1-ethanol, with a molar yield relative to butyraldehyde consumed of 59.2%, and 2-propyl-1,3-dioxalane with a yield in relation to butyraldehyde consumed of 23.8%. Besides the 30 g of 2-butoxy-1-ethanol and 11.85 g of

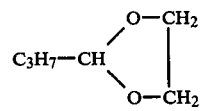

2.5 g (0.0338 moles) of normal butanol are formed. The amount of other impurities formed, namely ethyl butyrate, 1-2-dibutoxy ethane and dibutyl ether, is below 0.7 g, or 0.23% of the weight of the mixture of reactants.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. Process for the manufacture of a monether of monethylene glycol comprising hydrogenolysis of a 2-alkyl-1,3-dioxolane, with a co-catalytic system comprising palladium and an acid of phosphorous or a phosphoric ester of ethylene glycol and in the presence of ethylene glycol at a temperature and for a time sufficient to effect hydrogenolysis.

2. The process of claim 1, wherein the hydrogenolysis takes place at a temperature between about 100° to 250° C.

3. The process of claim 1 or 2, wherein the hydrogenolysis is carried out under a pressure of about 20 to 150 bars.

4. The process of claim 1 or 2, wherein the quantity of palladium varies from about 50 to 1500 ppm in relation to the mass of the mixture of 2-alkyl-1,3-dioxolane/ethylene glycol.

5. The process of claim 1 or 2, wherein the content of acid of phosphorous or of phosphoric ester of ethylene glycol calculated as $H_3PO_4$ varies between about 0.01 to 0.75% of the mass of the mixture of 2-alkyl-1,3-dioxolane and ethylene glycol.

6. The process of claim 1 or 2, wherein the molar ratio of ethylene glycol to 2-alkyl-1,3-dioxolane varies between about 1 to 15.

7. The process of claim 1 or 2, wherein the reaction takes place in the presence of a stabilizer of the hydroquinone family.

8. A process for the manufacture of a monether of monethylene glycol comprising hydrogenolysis of a dioxolane of the formula

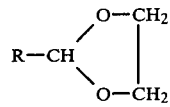

wherein R is hydrogen, a substituted or unsubstituted $C_1$-$C_8$ alkyl radical, a substituted or unsubstituted alicyclic radical, or an aromatic benzyl or tolyl group, said substituents having between 1 and 4 carbon atoms. With a co-catalytic system consisting essentially of palladium and a phosphoric acid in the liquid phase in the presence of ethylene glycol as the solvent and hydroquinone as a stabilizer; the hydrogenolysis temperature being between about 100° to 250° C., the pressure being from about 20 to 150 bars, and the molar ratio of ethylene glycol to dioxolane varying between about 1 to 15.

* * * * *